US008147899B2

(12) United States Patent
McMorrow et al.

(10) Patent No.: US 8,147,899 B2
(45) Date of Patent: Apr. 3, 2012

(54) METHODS AND SYSTEMS FOR DEPOSITING COATING ON A MEDICAL DEVICE

(75) Inventors: David McMorrow, Galway (IE); Timothy O'Connor, County Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1000 days.

(21) Appl. No.: 12/117,100

(22) Filed: May 8, 2008

(65) Prior Publication Data

US 2008/0280026 A1 Nov. 13, 2008

Related U.S. Application Data

(60) Provisional application No. 60/916,583, filed on May 8, 2007.

(51) Int. Cl.

| | |
|---|---|
| ***A61L 33/00*** | (2006.01) |
| ***B05D 3/00*** | (2006.01) |
| ***B05D 1/28*** | (2006.01) |
| ***B05C 11/00*** | (2006.01) |
| ***B05C 1/08*** | (2006.01) |

(52) U.S. Cl. ........ 427/2.25; 427/2.24; 427/429; 118/72; 118/260; 118/264; 118/268

(58) Field of Classification Search ................. 427/2.25, 427/2.24, 429; 118/72, 264, 260, 268
See application file for complete search history.

(56) References Cited

U.S. PATENT DOCUMENTS

| | | | | |
|---|---|---|---|---|
| 2005/0074544 | A1 | 4/2005 | Pacetti et al. | |
| 2006/0073265 | A1 | 4/2006 | Teichman et al. | |
| 2006/0110209 | A1 * | 5/2006 | Shekalim et al. | 401/208 |
| 2007/0281072 | A1 | 12/2007 | O'Connor et al. | |

FOREIGN PATENT DOCUMENTS

| | | |
|---|---|---|
| WO | 2005/091834 | 10/2005 |
| WO | 2008/054655 | 5/2008 |

OTHER PUBLICATIONS

International Search Report and Written Opinion, PCT/US2008/063000, Aug. 11, 2008.

* cited by examiner

*Primary Examiner* — Timothy J. Kugel
*Assistant Examiner* — Atnaf Admasu
(74) *Attorney, Agent, or Firm* — Vidas, Arrett & Steinkraus

(57) ABSTRACT

The present invention is directed to methods and systems for aligning and coating a medical device during a single coating cycle. A first section of an applicator may apply a contact force to surfaces of the medical device. The contact force may align and remove surface irregularities from the medical device prior to coating the medical device with coating. The coating may be resident on a second section of the applicator.

21 Claims, 6 Drawing Sheets

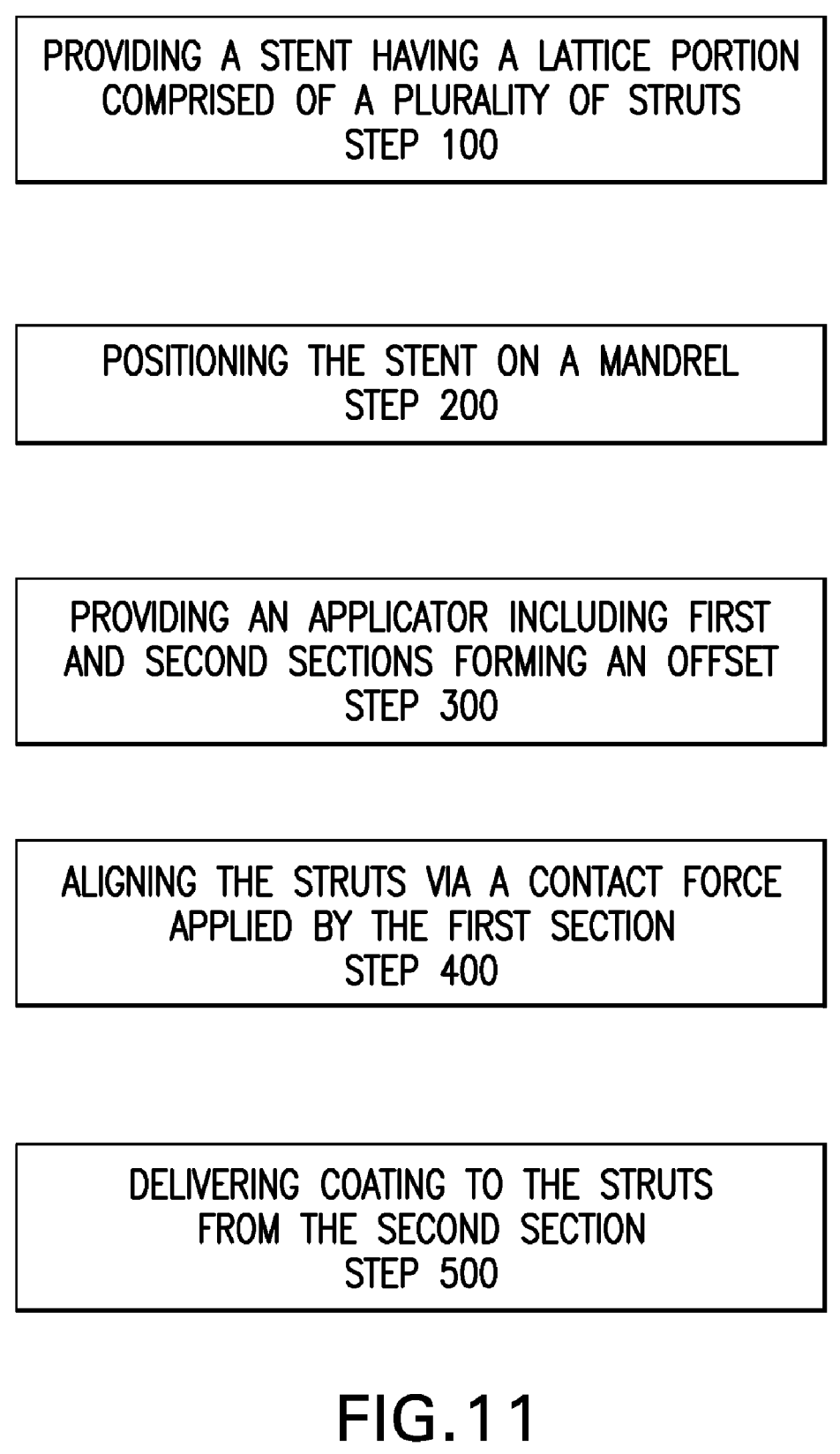

PROVIDING A STENT HAVING A LATTICE PORTION COMPRISED OF A PLURALITY OF STRUTS
STEP 100

POSITIONING THE STENT ON A MANDREL
STEP 200

PROVIDING AN APPLICATOR INCLUDING FIRST AND SECOND SECTIONS FORMING AN OFFSET
STEP 300

ALIGNING THE STRUTS VIA A CONTACT FORCE APPLIED BY THE FIRST SECTION
STEP 400

DELIVERING COATING TO THE STRUTS FROM THE SECOND SECTION
STEP 500

FIG. 11

METHODS AND SYSTEMS FOR DEPOSITING COATING ON A MEDICAL DEVICE

CROSS REFERENCE TO RELATED APPLICATION

The present application claims priority to U.S. provisional application Ser. No. 60/916,583 filed May 8, 2007, the disclosure of which is incorporated herein by reference in its entirety.

TECHNICAL FIELD

The present invention generally relates to the application of coating materials, comprising coating materials including therapeutic agent, to medical devices such as implantable stents. More specifically, the present invention includes coating systems and methods that transfer coating from an applicator to a medical device during the coating process.

BACKGROUND

The positioning and deployment of medical devices within a target site of a patient is a common, often repeated procedure of contemporary medicine. These devices, which may be implantable stents and other devices that may be deployed for short or sustained periods of time, may be used for many medical purposes. These can include the reinforcement of recently re-enlarged lumens, the replacement of ruptured vessels, and the treatment of disease, such as vascular disease by local pharmacotherapy, i.e., delivering therapeutic drug doses to target tissues while minimizing systemic side effects. The targeted delivery areas may include body lumens such as the coronary vasculature, peripheral vasculature, cerebral vasculature, esophagus, trachea, colon, biliary tract, urinary tract, prostate, and the like.

Coatings may be applied to the surfaces of these medical devices to increase their effectiveness. These coatings may provide a number of benefits including reducing the trauma suffered during the insertion procedure, facilitating the acceptance of the medical device into the target site, and improving the post-procedure effectiveness of the device.

Coated medical devices may also provide for the localized delivery of therapeutic agents to target locations within the body. Such localized drug delivery avoids the problems of systemic drug administration, producing unwanted effects on parts of the body that are not to be treated, or not being able to deliver a high enough concentration of therapeutic agent to the afflicted part of the body. Localized drug delivery may be achieved, for example, by coating portions of the medical devices that directly contact the inner vessel wall. This drug delivery may be intended for short and sustained periods of time.

BRIEF DESCRIPTION

The present invention is directed to methods and systems for aligning a medical device during a coating process. For example, a method in accordance with embodiments of the present invention may comprise providing a stent having a lattice portion comprised of a plurality of struts and positioning the stent on a mandrel. The method may include providing an applicator having first and second sections forming an offset. The method may further include aligning the struts via a contact force applied by the first section and delivering coating to the struts from the second section. This method may also include repeating the procedure, performing more or other steps, and adding additional layers of coating.

Embodiments of the present invention may also regard a system for coating a medical device. The system may include a mandrel to support and align the medical device, an applicator having first and second sections which form an offset, and a fluid source communicating with the second section. The first and second sections may form an offset. In the system, either or both the applicator and the medical device can be moved with respect to one another so that the first section applies a contact force to the medical device while the second section applies coating.

Embodiments of the present invention may still further regard a system for coating a medical device which includes a mandrel to support and align the medical device, an applicator having first and second sections along an edge, and a fluid source communicating with the second section. The first section may comprise a contact surface and the second section may comprise a plurality of recesses. In the system, either or both the applicator and the medical device can be moved with respect to one another so that the first section applies a contact force to the medical device while the second section applies coating.

The invention may be embodied by numerous methods and systems. The description provided herein, which, when taken in conjunction with the annexed drawings, discloses examples of the invention. Other embodiments, which incorporate some or all steps and systems as taught herein, are also possible.

BRIEF DESCRIPTION OF THE DRAWINGS

Referring to the drawings, which form a part of this disclosure:

FIG. 11 is a flow chart of methods that may be employed in accordance with embodiments of the present invention.

DETAILED DESCRIPTION

The present invention generally relates to methods and systems for aligning a medical device during a coating process.

These medical devices, which can be stents or other devices sized to be inserted into a patient, may be cut using a laser, injection molded, and/or assembled from wire. Stent production may result in surface misalignment and/or irregularities. Misalignment and/or irregularities of medical device surfaces may impact the coating process.

For example, in the case of an implanted stent, which are comprised of a plurality of stent struts which form a scaffolding structure, some of the struts may be burred, bowed, bent, and/or otherwise misaligned during production. Strut misalignment may limit the effectiveness of coating processes, such as in a roll coating process.

Methods and systems that embody the present invention may include an applicator configured to align and apply coating to a medical device in a single coating cycle.

Figure 1:
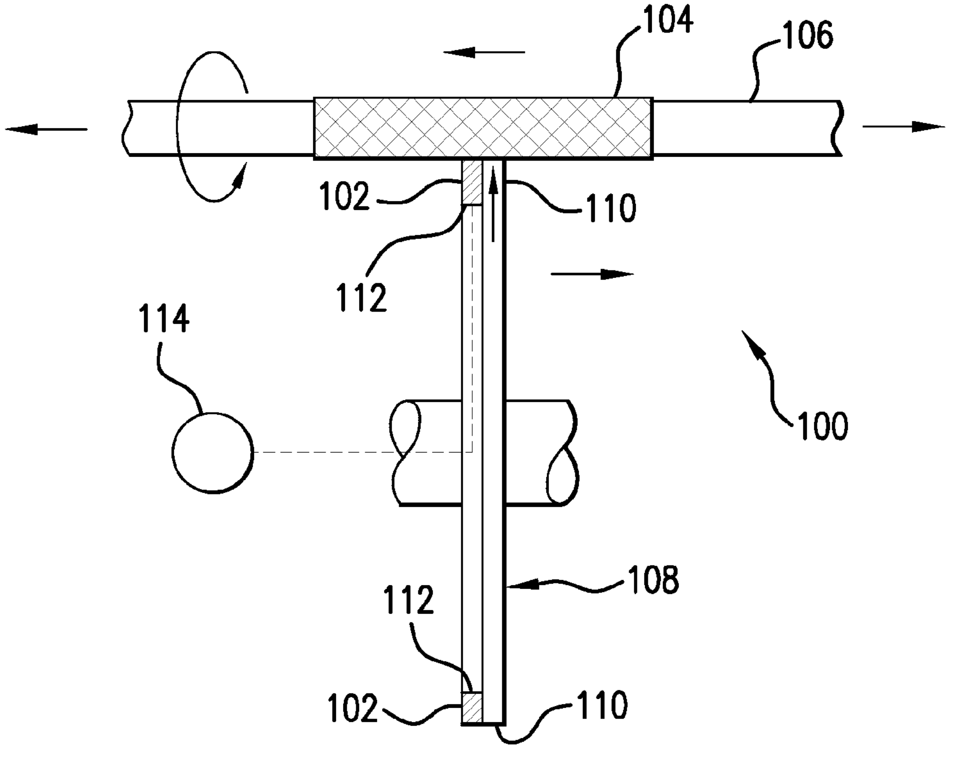
FIG. 1 shows a system for aligning and coating a medical device that may be employed in accordance with embodiments of the present invention.

Referring initially to FIG. 1, a system 100 for aligning and applying coating 102 to a medical device 104 is illustrated.

In this example, the system 100 includes a mandrel 106 configured to support and align the medical device 104, an applicator 108 having first and second sections 110, 112, which may form an offset along an edge of the applicator 108, and a fluid source 114 communicating with the second section 112.

Figure 2:
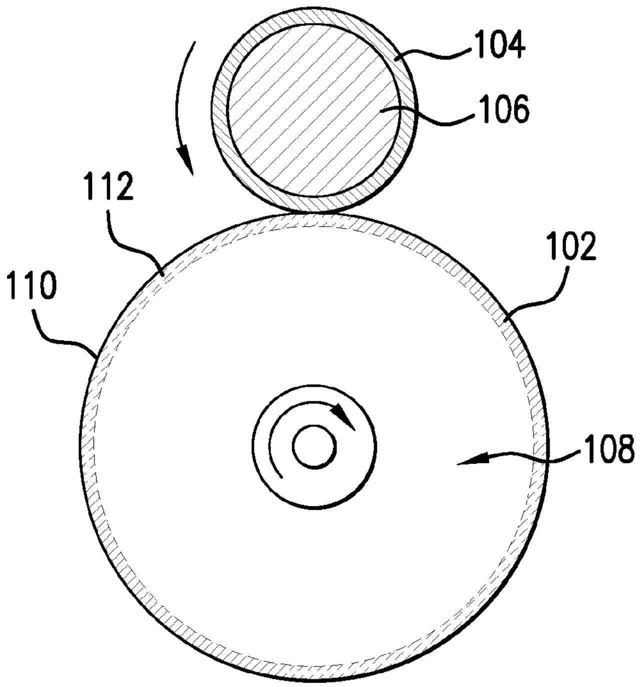
FIG. 2 shows an end view of the system of FIG. 1.

As seen in FIGS. 1-2, the medical device 104 may be positioned on the mandrel 106. The mandrel 106 may be rotatable and may move linearly, for example, via connection to a conventional machine tool (not shown). The mandrel 106 may be manufactured from any suitable material that is flexible and that can be placed under tension. For example, flexible materials that exhibit radial strength for tensioning may include, but are not limited to, stainless steel, annealed stainless steel, Kevlar™, and nylon. In addition, the mandrel 106 may be comprised of a central core made of one material and an outer layer or over-winding of other material(s) that may increase rigidity.

For instance, a steel core may be wound with aluminum and/or tungsten.

The outer diameter of the mandrel 106 may be slightly greater than the inner diameter of the medical device 104, thus, forming an interference fit. Therefore, during coating, the mandrel 106 can be placed under tension, thus imparting linear rigidity to the medical device 104, and therefore facilitating the axial alignment of the medical device 104 and mandrel 106.

Also seen in FIGS. 1-2 is the applicator 108. In this example, the applicator 108 is circular and includes first and second sections 110, 112 located along a circumferential edge. As seen in the figures, the first and second sections may be offset from one another. Although the applicator 108 shown in this example is circular, any suitable sizes and shapes may be used.

The first section 110 may contact the medical device 104 during the coating process to apply a contact force. The contact force applied by the first section 110 can act to axially align and straighten out struts or other portion of the medical device 104. As a result, misaligned surfaces and/or irregularities on surfaces of the medical device 104 may be removed or limited prior to the coating of the medical device 104. As can best be seen in FIG. 1, the first section 110 may be the leading edge of the applicator 108.

As seen in FIGS. 1-2, the second section 112 may be offset. For example, the second section 112 may be stepped down from the first section 110. Any sizes and shapes may be used for the offset. For example, the offset may be L-shaped. Further, a suitable height may be between approximately 10 and 20 microns. The first and second sections 110, 112 may also be any width. The width may depend upon the characteristics of the medical device. For example, when a stent strut is being coated, widths of approximately 200 microns, which is the width of some stent struts, may be suitable.

As best seen in FIG. 1, the second section 112 may be in fluid communication with a coating source 114. The coating source 114 can be used with conventional delivery systems (not shown), such as a hydraulic system, to deliver coating to the second section.

The system 100 of FIGS. 1-2 may be utilized for aligning and coating surfaces of a medical device 104 in one cycle. For example, as the first section 110 travels over the medical device to correct misaligned surfaces and/or irregularities on the medical device 104, the second section 112 can follow to deliver coating to the medical device 104 from the coating source 114.

Figure 3A:
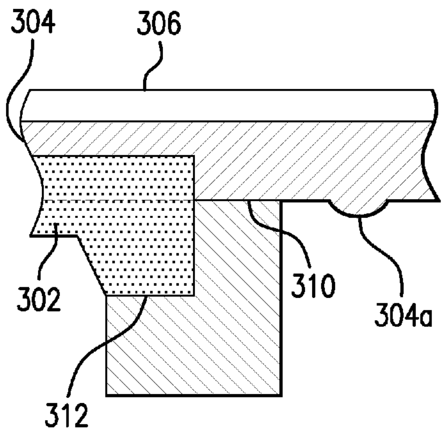
FIGS. 3*a-b* show enlarged cross-sectional views of an applicator of the system of FIG. 1 contacting the medical device and delivering coating in accordance with embodiments of the present invention.
Figure 3B:
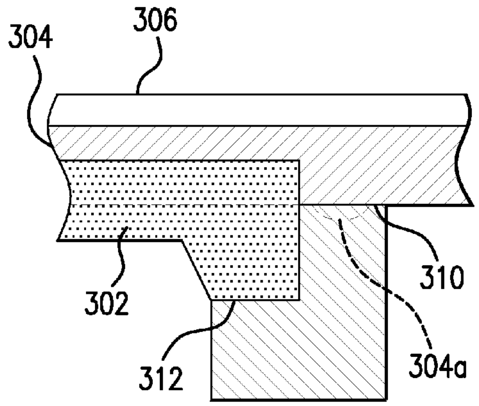

FIGS. 3*a-b* show an enlarged view of a medical device being coated with an applicator as may be employed with embodiments of the present invention. As illustrated in FIG. 3*a*, it can be seen that in this example the medical device 304, which is mounted on mandrel 306, has a burr 304*a*. Surface irregularities such as these may impact the coating process. Therefore, prior to applying coating 302, the first section 310 may apply a contact force to surfaces of the medical device 304 during a coating cycle. As can be seen in FIG. 3*b*, burr 304*a* may be realigned via the contact force (phantom lines illustrate where burr 304*a* previously existed). Following application of the contact force to a target surface, the second section 312 may apply coating 302 to the medical device 304. As seen in FIG. 3*b*, the thickness or height of the coating 302 may be slightly larger than the offset. For example, the coating 302 thickness may be a couple of microns larger than the height of the offset so that the medical device 304 can dip into the coating 302 to coat surfaces of the medical device 304 with a desired thickness.

Figure 4A:
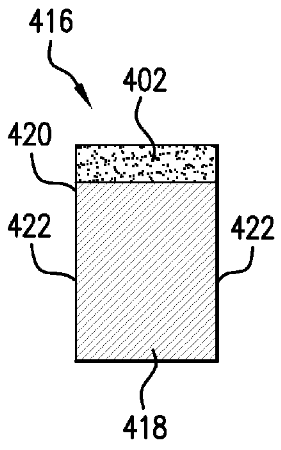
FIGS. 4*a-b* show cross-sectional views of stent struts and FIG. 4*c* shows a stent as may be coated in accordance with methods and systems of the present invention.

FIG. 4*a* is a side sectional view of a stent strut 416 as may be coated in accordance with embodiments of the present invention. The stent strut 416 shown in FIG. 4*a* has an inner surface 418, an outer surface 420, two cut faces 422, and a coating 402. As can be seen, the coating 402 covers only one surface of the strut 416. In this example, since the coating 402 is on the outer 420 or abluminal surface only, therapeutic loaded within the coating 402 can be limited to abluminal delivery. Other arrangements are possible.

Figure 4B:
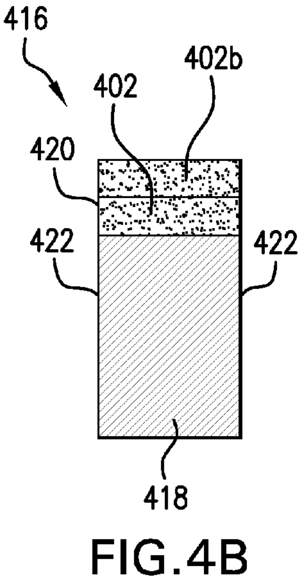

FIG. 4*b* shows another example of how coatings 402 may be applied in accordance with embodiments of the invention. In FIG. 4*b*, a first coating 402 and a second coating 402*b* have been applied to a stent strut 416. As can be seen, the first coating 402 is in contact with the outer surface 420 of the strut 416 while the second coating 402*a* is in contact with the first coating 402 and further covers the outer surface 420 of the strut 416. This second coating 402*a* may be applied in accord with the methods and systems of the present invention. It may also be applied with different methods and processes. In this example, as well as with the others described herein, if a second coating is employed this coating may comprise the same materials as the first coating and it may differ from the materials used for the first coating. In still other examples the coating may be applied in other patterns as well. For example, it may be applied to the inner surface and not the outer surface, likewise it may be applied to both the inner and outer surfaces if desired. In a exemplary embodiment, the outer surface is coated and the two cut faces as well as the inner surface are not.

Figure 4C:
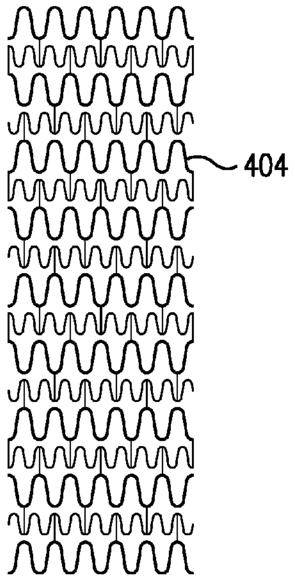

FIG. 4*c* shows a side view of a stent 404 as may be aligned and coated in accordance with embodiments of the present invention. A coating or coatings may be applied to portions of or along the entire length of the stent 404. The struts shown in FIG. 4*a*-*b* are struts that may comprise and make up this stent 404.

The stent 404 of FIG. 4*c* may be self-expanding, mechanically expandable, or a hybrid stent which may have both self-expanding and mechanically expandable characteristics. The stent may be made in a wide variety of designs and configurations, and may be made from a variety of materials including plastics and metals.

While the workpiece shown in this figure is a stent, many other medical devices may be coated in accord with the methods of the present invention. For example, other medical devices that may be coated include filters, grafts, and other devices used in connection with therapeutic coatings.

Figure 5:
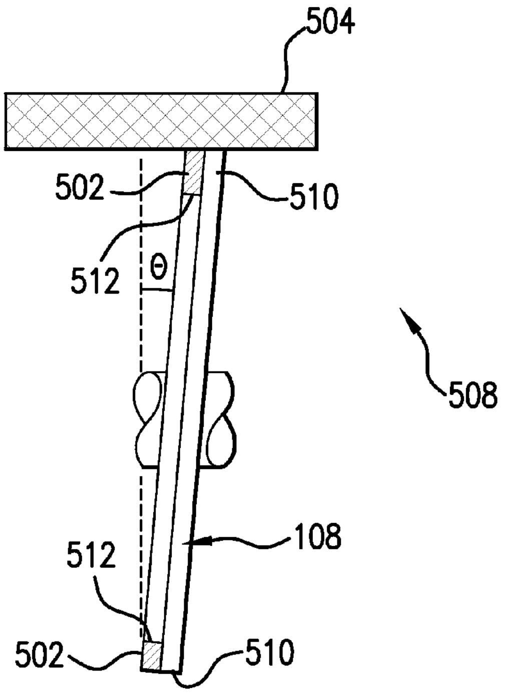
FIG. 5 shows an applicator that may be arranged at an angle as may be employed in accordance with embodiments of the present invention.

FIG. 5 shows another applicator 508 that may be used in accordance with embodiments of the present invention. In this system, the applicator 508 may be arranged at an angle.

The applicator 508 may be disposed at any suitable angle, for instance, acute angles between 1-5° degrees may be used. In this example, since the applicator 508 may be disposed at an angle, the second section 512 of the applicator 508 may apply coating 502 in a helical pattern to the medical device 504. In addition, in some instances, a regulating wheel (not shown) can also be provided. The medical device 504 may be positioned between the applicator 508 and the regulating wheel. The medical device 504 may be rotated about its axis between the applicator 508 and the regulating wheel due to the inclination of the applicator 508 relative to the regulating wheel. For example, such an arrangement may be similar to that used in a conventional centerless grinding operation.

Figure 6:
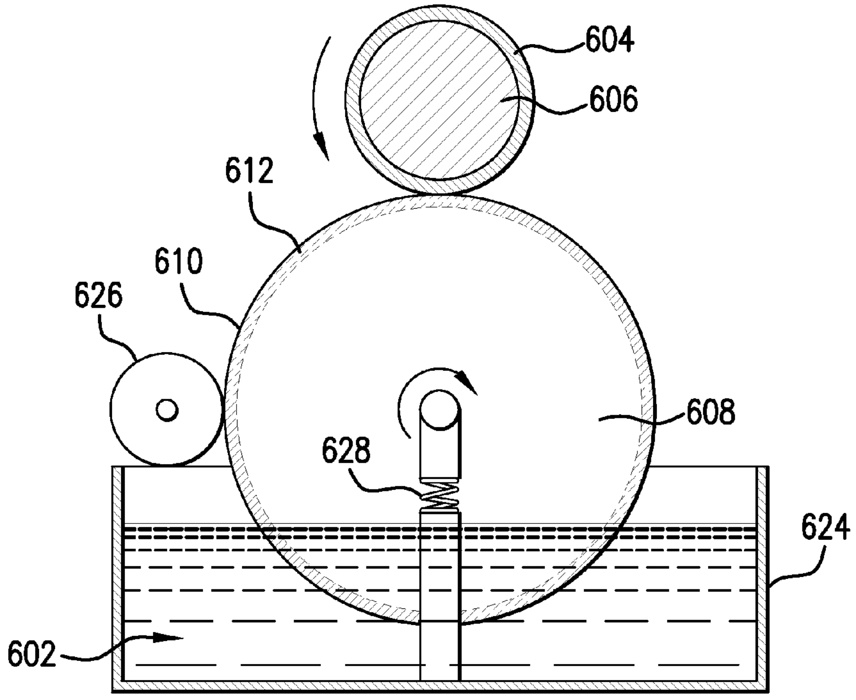
FIG. 6 shows applicator being rotated through a vat as may be employed in accordance with embodiments of the present invention.

As shown in FIG. 6, embodiments of the present invention may also employ an applicator 608 that may be rotated through a vat 624 to deposit coating 602 on the second section 612. In the example of FIG. 6, the applicator 608 is being rotated through a vat 624 containing coating 602 and the second section 612 accumulates coating on a surface thereof. Then, the applicator 608 may pass a metering device 626 that may regulate the thickness of the coating 602 on the second section 612 prior to applying the coating 602 to the medical device 604. Also as seen in FIG. 6, the first section 610 of the applicator 608 may be biased towards the medical device by any suitable biasing member 628, such as, for example, via a spring, pneumatic cylinder, and/or hydraulic cylinder. Other arrangements are possible. For instance, in other examples, the mandrel 606 may be biased towards the applicator 608.

Figure 7:
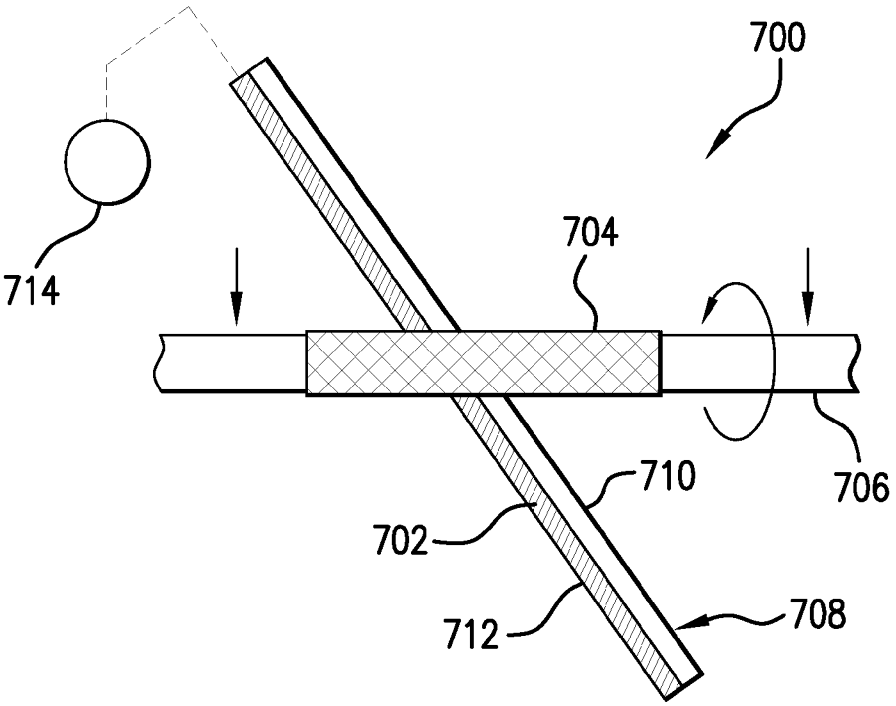
FIG. 7 shows a flat rod applicator that may be employed in accordance with embodiments of the present invention.

FIG. 7 shows another system 700 for aligning a medical device 704 during a coating process in accordance with embodiments of the present invention. In this exemplary embodiment, the L-shaped applicator 708 may have first and second sections 710, 712, which form an offset located along an edge thereof. The second section 712 may be in communication with a fluid source 714. As seen in FIG. 7, the applicator 708 may remain stationary during the coating process.

The mandrel 706 may be rotated and moved linearly across the applicator 708. As the mandrel 706 is moved, the first section 710 may apply a contact force to surfaces of the medical device 704 while the second section 712 may apply coating 702. As may also be seen in this example, the applicator 708 may be arranged on a work surface at an angle, however, other arrangements are possible.

Figure 8:
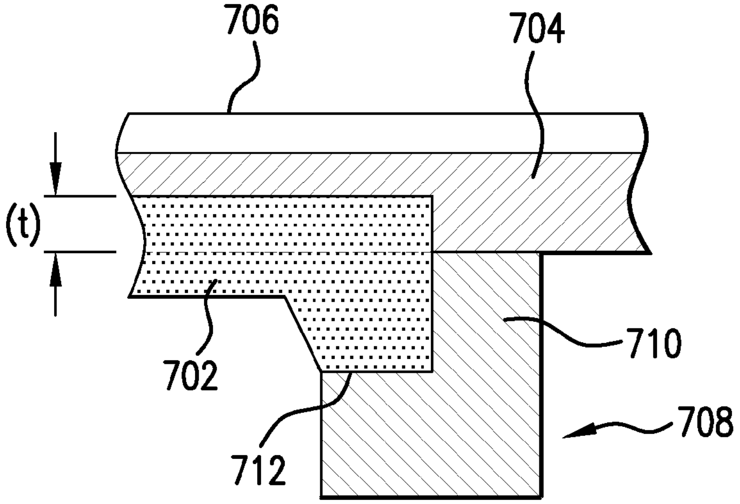
FIG. 8 shows an enlarged cross-sectional view of the applicator of the system of FIG. 7 contacting the medical device and delivering coating in accordance with embodiments of the present invention.

FIG. 8 shows an enlarged view of the medical device 704, mandrel 706, and the first and second sections 710, 712 of the applicator 708. As seen in FIG. 8, the coating 702 thickness or height (t) may be slightly larger than the offset formed by the first and second sections 710, 712 of the applicator 708. Consequently, the medical device 704 may dip into the coating 702 as the medical device 704 moves over the applicator 708 to coat the medical device 704 with a desired coating thickness.

Figure 9:
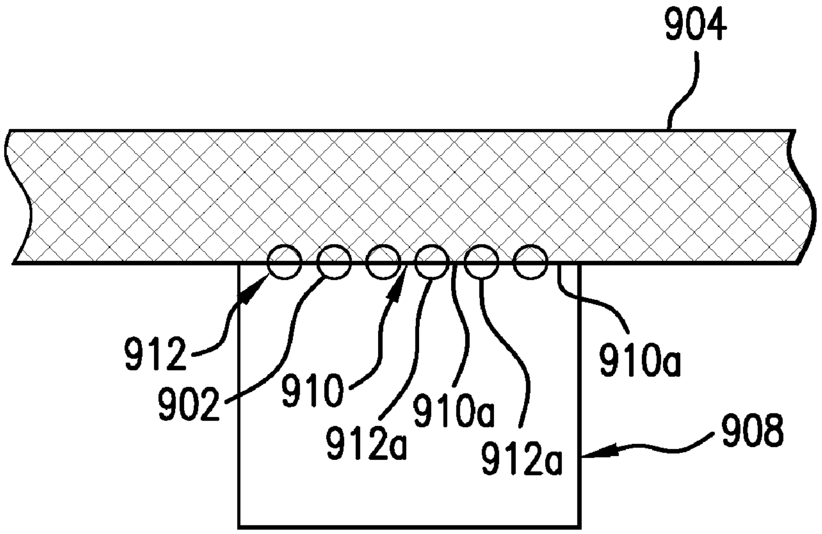
FIG. 9 shows an applicator having a first section with a plurality of contact surfaces located between a plurality of second sections as may be employed in accordance with embodiments of the present invention.
Figure 10:
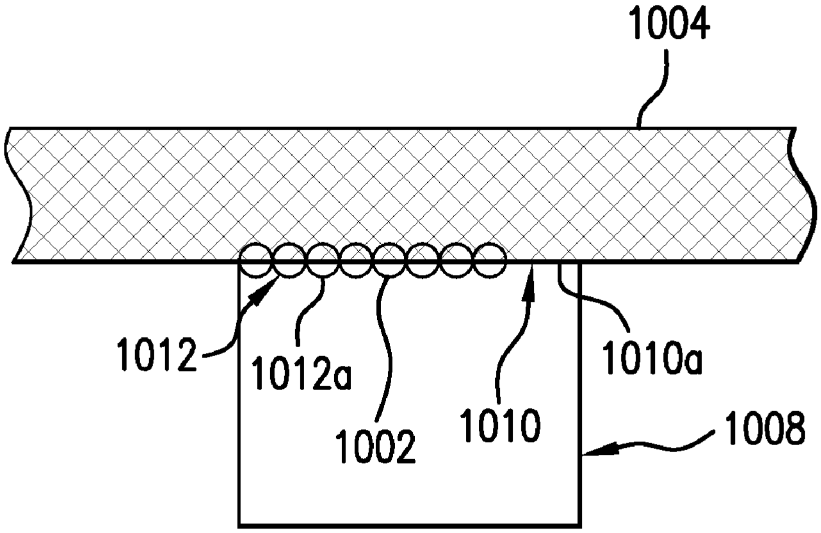
FIG. 10 shows an applicator having a first section with a contact surface and a second section with a plurality of recesses as may be employed in accordance with embodiments of the present invention.

FIGS. 9 and 10 illustrate examples of additional applicators 908, 1008 which may be used in accordance with the embodiments of the present invention. The applicators 908, 1008 of FIGS. 9 and 10 may be used with the methods and systems described herein above with reference to FIGS. 1-3 and 5-7 and/or other methods and systems.

FIG. 9 shows an applicator 908 having first and second sections 910, 912. The first section 910 may be comprised of a plurality of contact surfaces 910*a*. The second section 912 may be comprised of a plurality of recesses 912*a*. The plurality of contact surfaces 910*a* are located in between the plurality of recesses 912*a*. The plurality of contact surfaces 910*a* may apply contact forces to the medical device 904 to align the device while the plurality of recesses may apply coating 902 to the medical device 904.

FIG. 10 shows an applicator 1008 having first and section sections 1010, 1012. The first section 1010 may be comprised of a contact surface 1010*a*. The second section 1012 may be comprised of a plurality of recesses 1012*a*. The contact surface 1010*a* may be located adjacent to the plurality of recesses 1012*a* on a leading edge of the applicator 1008. The contact surface 1010*a* may apply contact forces to the medical device 1004 to align the device while the plurality of recesses may apply coating 1002 to the medical device 1004.

FIG. 11 shows a flow chart including method steps that may be employed with embodiments of the present invention for aligning and coating a stent during a single coating cycle. In the example of FIG. 11, step 100 may include providing a stent having a lattice portion comprised of a plurality of struts. Step 200 may include positioning the stent on a mandrel. Step 300 can include providing an applicator including first and second sections forming an offset. Step 400 may include aligning the struts via a contact force applied by the first section. Step 500 may include delivering coating to the struts from the second section.

In alternative embodiments, not shown, the sequence of steps may be reordered and steps may be added or removed. The steps may also be modified.

While various embodiments have been described, other embodiments are plausible. It should be understood that the foregoing descriptions of various examples of the applicator are not intended to be limiting, and any number of modifications, combinations, and alternatives of the examples may be employed to facilitate the effectiveness of aligning and application of coating to the medical device.

Coatings that may be used with embodiments of the present invention, may comprise a polymeric and/or therapeutic agent formed, for example, by admixing a drug agent with a liquid polymer, in the absence of a solvent, to form a liquid polymer/drug agent mixture. The coatings may also be polymer free. A suitable list of drugs and/or polymer combinations is listed below. The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, everolimus, zotarolimus, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Coatings used with embodiments of the present invention may comprise a drug agent or a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

Coatings from polymer dispersions such as polyurethane dispersions (BAYHYDROLR®, etc.) and acrylic latex dispersions may also be used with the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method for coating a stent, the method comprising the steps of:
- providing a stent having a lattice portion comprised of a plurality of struts;
- positioning the stent on a mandrel;
- providing an applicator including first and second sections forming an offset;
- aligning the struts via a contact force applied by the first section; and
- delivering coating to the struts from the second section.

2. The method of claim 1 further comprising applying tension to the mandrel to axially align the medical device.

3. The method of claim 1 wherein the contact force and coating are applied to an outer surface of the medical device.

4. The method of claim 1 wherein the first section contacts the medical device at an acute angle.

5. The method of claim 1 wherein applicator is substantially circular shaped and the first and second sections are located on a circumferential edge thereof.

6. The method of claim 5 wherein the applicator is rotatable.

7. The method of claim 6 wherein the applicator moves linearly with respect to a longitudinal axis of the stent.

8. The method of claim 1 wherein the first section is comprised of a contact surface and the second section is comprised of a plurality of recesses.

9. The method of claim 8 wherein the first section is a plurality of contact surfaces located between the plurality of recesses.

10. The method of claim 1 wherein the applicator is a substantially square shaped rod.

11. The method of claim 10 wherein the rod is stationary and the mandrel is rotatable and moves linearly with respect to the rod.

12. The method of claim 1 wherein the mandrel is rotatable and configured to move linearly with respect to a longitudinal axis of the stent.

13. The method of claim 1 wherein the applicator is configured to rotate the stent about the mandrel.

14. A system for coating a medical device, comprising:
- an applicator having first and second sections which form an offset, the first and second sections are located along an edge of the applicator; and
- a fluid source communicating with the second section;
- wherein at least one of the first and second sections of the applicator and the medical device move with respect to one another so that the first section applies a contact force to the medical device while the second section applies a coating.

15. The system of claim 14 wherein the applicator is a flat rod.

16. The system of claim 14 wherein the applicator is stationary and the medical device is moved with respect to the flat rod.

17. The system of claim 14, wherein the applicator is a circular shaped disc.

18. The system of claim 14, further comprising a mandrel configured to support and align the medical device.

19. A system for coating a medical device, comprising:
- an applicator having first and second sections located along an edge, the first section forms a contact surface and the second section is comprised of a plurality of recesses; and
- a fluid source communicating with the second section;
- wherein at least one of the first and second sections of the applicator and the medical device move with respect to one another so that the first section applies a contact force to the medical device while the second section applies a coating.

20. The system of claim 19, wherein the first section is a plurality of contact surfaces located in between the plurality of recesses.

21. The system of claim 19, further comprising a mandrel configured to support and align the medical device.

* * * * *